(12) United States Patent
Bhattacharya

(10) Patent No.: US 9,739,894 B2
(45) Date of Patent: Aug. 22, 2017

(54) GAMMA CAMERA DEAD TIME COMPENSATION USING A COMPANION RADIOISOTOPE

(71) Applicant: Siemens Medical Solutions USA, Inc., Malvern, PA (US)

(72) Inventor: Manojeet Bhattacharya, Chicago, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 14/964,710

(22) Filed: Dec. 10, 2015

(65) Prior Publication Data

US 2016/0356894 A1    Dec. 8, 2016

Related U.S. Application Data

(63) Continuation-in-part of application No. PCT/IB2015/054323, filed on Jun. 8, 2015.

(51) Int. Cl.
  *G01T 1/17*      (2006.01)
  *A61B 6/03*      (2006.01)
  *G01T 1/161*     (2006.01)

(52) U.S. Cl.
  CPC ............ *G01T 1/171* (2013.01); *A61B 6/037* (2013.01); *G01T 1/161* (2013.01)

(58) Field of Classification Search
  CPC ............ G01T 1/17; G01T 1/161; A61B 6/03
  See application file for complete search history.

(56) References Cited

U.S. PATENT DOCUMENTS

| | | | | |
|---|---|---|---|---|
| 4,771,177 A | * | 9/1988 | Brown | G01T 1/1642 250/252.1 |
| 4,882,494 A | * | 11/1989 | Rogers | G01T 1/1642 250/252.1 |
| 5,461,232 A | * | 10/1995 | McCandless | A61B 6/037 250/363.04 |
| 5,990,482 A | * | 11/1999 | Bertelsen | G01T 1/1648 250/252.1 |
| 6,008,493 A | * | 12/1999 | Shao | G01T 1/1611 250/363.04 |
| 6,140,649 A | * | 10/2000 | Lonn | G01T 1/1648 250/363.02 |

(Continued)

FOREIGN PATENT DOCUMENTS

| | | |
|---|---|---|
| EP | 0444324 | 9/1991 |
| GB | 2463707 | 3/2010 |

(Continued)

OTHER PUBLICATIONS

Lindstrom, R.; Fleming, R., "Dead Time, Pileup, and Accurate Gamma-Ray Spectrometry" Radioactivity and Radio-chemistry, pp. 20-27, vol. 6, No. 2, 1995.

(Continued)

*Primary Examiner* — Marcus Taningco

(57) ABSTRACT

For dead time compensation, a point source with a same radioisotope as used for the radiopharmaceutical is positioned by the detector. Counts from the point source without the patient and with the patient are used to correct the system or detector sensitivity. Reconstruction is performed with the sensitivity normalized for count rate, compensating for the dead time and spectral broadening.

24 Claims, 2 Drawing Sheets

(56) References Cited

U.S. PATENT DOCUMENTS

| | | | | |
|---|---|---|---|---|
| 6,194,724 B1* | 2/2001 | Raji | ............... | G01T 1/1615 |
| | | | | 250/363.04 |
| 6,281,504 B1* | 8/2001 | Takayama | ............ | G01T 1/1648 |
| | | | | 250/363.04 |
| 2007/0221850 A1* | 9/2007 | Panin | ............... | G01T 1/1617 |
| | | | | 250/363.04 |
| 2012/0324648 A1* | 12/2012 | Amano | ............... | A61B 6/037 |
| | | | | 5/601 |
| 2014/0371580 A1 | 12/2014 | Bhattacharya | | |

FOREIGN PATENT DOCUMENTS

| | | |
|---|---|---|
| WO | 9954754 | 10/1999 |
| WO | 2008088386 | 7/2008 |

OTHER PUBLICATIONS

EP Search Report dated Oct. 7, 2016 from counterpart EP application No. 16172937.1-1559.

\* cited by examiner

GAMMA CAMERA DEAD TIME COMPENSATION USING A COMPANION RADIOISOTOPE

CROSS-REFERENCE TO RELATED APPLICATION

This application is a continuation-in-part of PCT/IB2015/054323 filed on Jun. 8, 2015, the contents of which are incorporated by reference.

BACKGROUND

The present embodiments relate to single photon emission computed tomography (SPECT). In particular, the present embodiments relate to dead time compensation in SPECT.

During SPECT imaging, the detector electronics take time to perform detection of an emission. During this period, additional emissions are not detected due to the unavailability of the detector electronics. As a result, the actual emissions may be under counted. The count of detected emissions is corrected for system dead time. In one approach, a signal is input at fixed frequency and amplitude to the detector electronics. Due to the fixed frequency, a known number of signals is input. Due to dead time from detecting emissions from the patient, some of the fixed frequency signals are not detected. The ratio of detected ones of the fixed frequency to the input number provides a measure of dead time. The count of detected emissions from the patient is divided by the ratio to correct for the dead time.

Since the fixed frequency signal is input at the electronics, any contribution of the detection system before signal processing to the dead time is ignored. This contributes to uncertainty in the reconstructed image. In quantitative SPECT, an inexact correction may result in an inexact quantification. When imaging therapy isotopes with corresponding high-count rates, the inaccuracy may be more significant. These approaches also require that the processing is independent of the pulse height, which may not be the case. High count rates during imaging may lead to spectral broadening, which also results in undercounting in the preset energy window due to change in resolution.

BRIEF SUMMARY

By way of introduction, the preferred embodiments described below include methods, systems, and non-transitory computer readable media for dead time compensation. A point source with a same radioisotope as used for the radiopharmaceutical is positioned by the detector. Counts from the point source without the patient and with the patient are used to correct the system or detector sensitivity. Reconstruction is performed with the sensitivity normalized for count rate, compensating for the dead time and spectral broadening.

In a first aspect, a method is provided for dead time compensation for a gamma camera. The gamma camera detects a first count rate from a calibrated radioisotope source connected adjacent to the gamma camera. The detecting of the first count rate is performed without emissions from a patient. The gamma camera detects a second count rate from the radioisotope source. The detecting of the second count rate is performed during detection of the emissions from within a patient, and the emissions are from a same radioisotope as the radioisotope source but within the patient. A sensitivity is corrected as a function of the first and second count rates. The emissions are reconstructed as a function of the corrected sensitivity. An image is generated from the reconstruction.

In a second aspect, a single photon emission computed tomography (SPECT) system includes a gamma camera. A shielded and calibrated point source connects at the gamma camera to emit radiation from a radioisotope in the shielded point source. Detection electronics are configured to detect emissions, including the radiation from the shielded point source and radioisotope emissions from a patient. The radioisotope emissions from the patient are from a same radioisotope as the radioisotope in the shielded point source. A processor is configured to compensate for dead time of the detection electronics. The compensation is a function of real-time detection of the radiation from the shielded point source.

In a third aspect, a method is provided for correction of an emission detector. A detector detects first emissions from a patient and second emissions from a point source. The second emissions are subjected to dead time from the detection of the first and second emissions, and the first and second emissions are from a same radioisotope. A processor corrects for a reconstruction from the first emissions. The correcting is a function of a count of the second emissions.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Rather than measuring the system dead time, system sensitivity is normalized as a function of the count rate from the shielded point source of the same radioisotope. The sensitivity normalization using counts from a point source does not depend on the assumption that the detector signal processing is independent of pulse height as the pulse heights of the signals from the patient and the radioisotope of the point source are identical. By imaging a calibrated and shielded point source of a same radioisotope as the radiopharmaceutical being imaged for a patient, the broadening or pulse height constraint may be avoided. The sensitivity normalization also compensates, at least in part, for the dead time. This approach may be used for any isotope, count rate, collimator, gamma camera, detector electronics, or system. Rather than normalizing sensitivity, this dead-time compensation factor may also be used to correct projection data or the data model.

Figure 1:
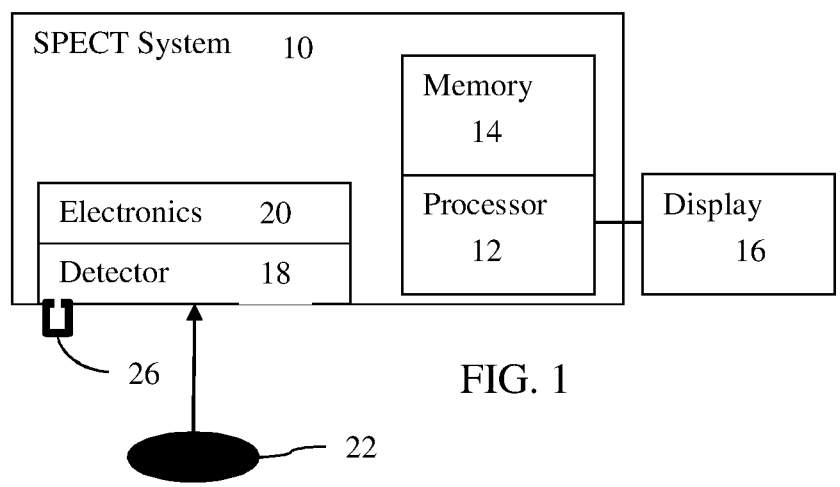
FIG. 1 is a block diagram of a SPECT system, according to one embodiment, with dead time compensation.

FIG. 1 shows one embodiment of a single photon emission computed tomography (SPECT) system 10 for sensitivity normalization and/or to compensate for dead time. The system 10 includes a processor 12, a memory 14, a display 16, a detector 18, detector electronics 20, and a shielded source 26. The processor 12, memory 14, and/or display 16 are part of the SPECT system 10 or are separate (e.g., a computer or workstation). Additional, different, or fewer components may be provided. For example, user input, patient bed, computed tomography system, or other SPECT related devices are provided. Other parts of the system may include power supplies, communications systems, and user interface systems. Any now known or later developed SPECT system 10 may be used. As another example, the display 16 is not provided.

The detector 18 is a gamma camera connected with a gantry. The gamma camera may include the detector circuits 20 and the detector 18, or just the detector 18. The gamma camera is a planar photon detector, such as having crystals or scintillators with photomultiplier tubes or other optical detector. The gantry rotates the gamma camera about the patient. During scanning of a patient, emission events are detected at different locations on the camera while at different positions or angles relative to the patient.

The detector 18 has any shape. For example, the detector 18 has a square or rectangular detection surface in a plane orthogonal to the patient. Other shapes may be used.

Figure 2:
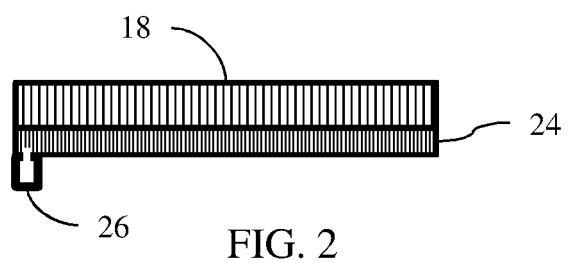
FIG. 2 is a cross-sectional side view of one embodiment of a detector and collimator with an added long-lived point source.

Referring to FIG. 2, a collimator 24 is positioned in front of, adjacent to, or by the detector 18. The collimator 24 is part of or connected to the detector 18. The collimator 24 includes lead, tungsten, or other material that is impervious to or absorbs and attenuates gamma radiation. The collimator 24 includes holes or other structures that pass gamma radiation from some directions (e.g., more orthogonal) and limit radiation from directions at other angles.

A shielded point source 26 is positioned relative to the detector 18. The shielded point source 26 is shielded in lead, tungsten, or other material preventing or limiting exposure to the patient. The shield may have a hole, window, or gap in shielding for allowing emissions of gamma rays from the point source 26 to impinge upon the detector 18. Any size point source 26 may be used, such as a 1 mm$^3$ vessel with the radioisotope. Line or other shaped sources may be used.

The shielded point source 26 is connected to emit radiation at the detector 18 in a repeatable or known position. The connection is by weld, bolt, latch, press fit, threading, or other connection to the collimator 24, detector 18, gantry, frame, or other structure. The shielded point source 26 may be added to an existing detector 18 or collimator 24, such as adding a bracket to attach the point source 26 to a frame holding the detector 18. The shielded point source 26 may be designed to fit in or be part of the collimator 24. For example, a threaded hole is formed in the collimator 26. The shield of the shielded point source 26 includes matching threads for attaching. The vessel may be replaced and/or refilled, such as for each patient or daily.

The connection positions the shielded point source 26 so that the hole or window in the shielding is directed at the detector 18. The positioning angles the point source 26 to pass gamma emissions through the collimator 24 to the detector 18.

The point source 26 is positioned anywhere in front of the detector 18. In one embodiment, the point source 26 is positioned at a corner or other region that may not detect many gamma rays from the patient. Due to the collimation and relative position to the patient, the edge or corner of the detector 18 may be less likely to detect emissions from the patient. As a result, the shielded point source 26 is less likely to interfere with detection of emissions from the patient 22. Due to size, the point source 26 exposes or covers a small part (e.g., less than 1%) of the detector 18. The point source 26 is placed against or in the collimator 24 or is spaced from the collimator 24.

A radioisotope in the point source 26 emits radiation at the gamma camera. The point source 26 includes radiopharmaceutical that is of the same type or mixture ingested or used by the patient. The same radiopharmaceutical is divided, with some being placed in the point source 26 and other being used for the patient. Alternatively, a factory-calibrated source of the same radioisotope but not in radiopharmaceutical form is used. A liquid, gel, or solid with the same radioisotope as used for imaging the patient is positioned in a vessel as the point source 26. For example, $^{177}$Lu is used for both the point source 26 and the radiopharmaceutical.

The radioisotope of the point source 26 has a same or different strength as the radioisotope of the radiopharmaceutical. In one embodiment, the source strength for the point source 26 is less by a factor of 2 or more (e.g., 10 or more) than the source strength of the radiopharmaceutical. The same radioisotope is used, but at a different strength. For example, the strength for the patient is about 100 millicurie while the strength for the point source 26 is at about 2-3 millicurie. The source strength is chosen such that the strength of the point source 26 does not significantly add to the system count rate and such that the system dead time during count rate determination in the absence of the patient is negligible. The point source 26 is calibrated with a dose calibrator.

The detector electronics 20 include pulse arithmetic circuits, pulse height analyzer, digitizer, filter, analog-to-digital converter, application specific integrated circuit, field programmable gate array, signal processor, combinations thereof, processor 12, or other now known or later developed circuit for detecting the position and energy of each emission on the detector 18. A processor may be provided for pile-up handling. The detector electronics 20 receive the output of the photomultiplier tubes or other light detector of the detector 18 and output a position, time, and energy level. The detector electronics 20 may include a threshold function, filter, or other process for rejecting emissions due to unresolvable pile-up or energy not in an expected window or range for the radioisotope.

The detector electronics 20 detect emissions including the radiation from the shielded point source 26 and radioisotope emissions from a patient 22. Using a radioisotope marker (i.e., point source 26) for dead time compensation during the patient acquisition may not require any modifications to detector electronics 20.

The detector electronics 20 may apply an energy range filter to detect emissions from either or both the patient and point source 26. For example, the radioisotope for the patient and point source 26 is Tc-99m with peak energy of emissions at 140 keV. By detecting the energy as being within 10% or other range of 140 keV, emissions are detected. The detector electronics 20 or other processor counts the number of emissions for a given energy range. The count is an absolute count or is a count rate (i.e., number of emissions per unit time). Emissions with energies outside the ranges are not counted or are discarded.

A region of interest relative to the point response function is determined for detections from the point source location on the detector 18. A range within or of the point spread function is used. The region of interest is centered in the point response. Response outside of the region of interest is ignored or discarded. During a patient scan using the same radioisotope, the extended regions of the point response function for the point source 26 may be contaminated by photons from the patient. The region of interest reduces the contamination. The same region of interest is applied for emissions detected with and without the patient being present.

The same detector 18 and detector electronics 20 are used to detect emissions when the patient or other object is not positioned for SPECT scanning. The emissions are from, for the most part, just the point source 26. The detector electronics 20 apply the same energy range filter to count emissions as when the patient is being scanned. Since the radioisotope for the point source 26 and the radiopharmaceutical are the same, the same energy range filter is applied. In alternative embodiments, the energy ranges and/or regions of interest in the point spread function may be overlapping but different.

The detection by the detector 18 and detector electronics 20 occurs during a scanning session for a patient 22. The patient 22 is positioned within the gantry or on a bed of the SPECT system 10. For imaging uptake in a patient, the detector 18 detects emissions from the patient 22. The emissions occur from any location in a finite source (i.e., the patient 22). The radiotracer (i.e., radiopharmaceutical) in the patient migrates to, connects with, or otherwise concentrates at specific types of tissue or locations associated with specific biochemical reactions. As a result, a greater number of emissions occur from locations of that type of tissue or reaction. For example, the radiotracer is designed to link with locations of glucose uptake, fatty acid synthesis, or other metabolic process. A given imaging session occurs during one scanning appointment and/or ingestion or injection of the radiotracer for a given instance of SPECT imaging.

The same or different point source 26 may be used for the blank scan without the patient and the patient scan. The point source or point sources 26 are calibrated using a dose calibrator.

In one embodiment, the detector electronics 20 performs pile-up separation. Emissions may occur rapidly enough in sequence that energy from one emission may result in a later emission appearing to have higher energy. By separating out the emissions and accounting for pile-up, emissions at the desired energies may be more accurately determined without discarding actual emissions that should be maintained. In another embodiment, the pile-up processing is not used. Instead, the detector electronics 20 are operated without pile-up separation. A fully integrated mode (i.e., detect based on energy without attempting to account of energy tails from other emissions) is used.

The processor 12 is a general processor, digital signal processor, graphics processing unit, application specific integrated circuit, field programmable gate array, digital circuit, analog circuit, combinations thereof, or other now known or later developed device for processing emission information. The processor 12 is a single device, a plurality of devices, or a network. For more than one device, parallel or sequential division of processing may be used. Different devices making up the processor 12 may perform different functions, such as one processor (e.g., application specific integrated circuit or field programmable gate array) for reconstructing and another for compensating for dead time or normalizing sensitivity. In one embodiment, the processor 12 is a control processor or other processor of the SPECT system 10. In other embodiments, the processor 12 is part of a separate workstation or computer.

Figure 3:
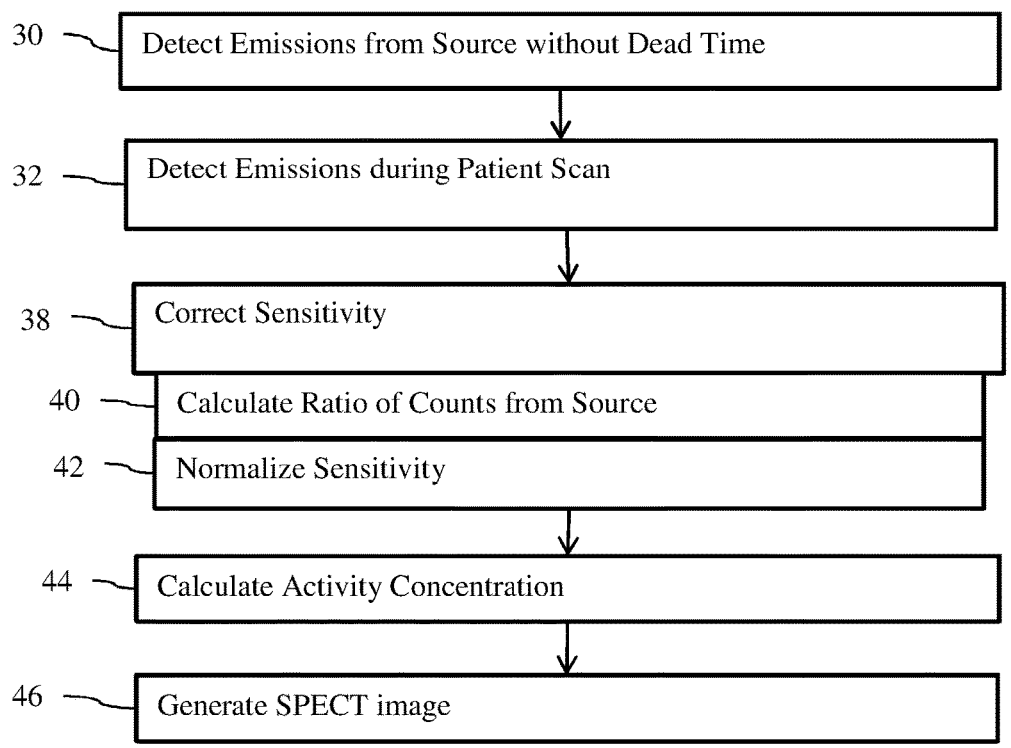
FIG. 3 is a flow chart diagram of one embodiment of a method for dead time compensation.

The processor 12 operates pursuant to stored instructions to perform various acts described herein, such as performing acts 38, 44 and 46 of FIG. 3. The processor 12 is configured by software, firmware, and/or hardware to perform, control performance, and/or receive data resulting from any or all of the acts of FIG. 1.

In one embodiment, the processor 12 is configured to compensate for dead time of the detector electronics 20. During the detection processing, the detector electronics 20, of which the processor 12 may be part, cause a delay. Any emissions occurring during the delay are not processed or are not detected. This delay of nanoseconds or microseconds is the dead time. To compensate for the dead time, the processor 12 determines a scaling factor to apply to sensitivity.

In one embodiment, the processor 12 uses the real-time detection of the radiation from the shielded point source 26 for the compensation. The count of the emissions from the shielded point source 26 is used. Since these emissions from the point source 26 are detected while also performing operations to detect the emissions from the patient with the same detector, the emissions from the point source 26 are subject to the dead time of the detector electronics 20. The spectrum may broaden due to detecting a larger number of emissions, so smaller fraction of the peak may be detected in the energy window. As a result, the number of detected emissions or counts is lower for reasons other than dead time.

To determine the compensation, the number of emissions from another calibrated point source 26 is measured prior to placement of the patient within the SPECT system 10. The emissions from the point source 26 are measured when there are no emissions from a radiotracer in a patient. The measured count from the detector 18 with no or little dead time and no spectral broadening is stored in the memory 14 for use in dead time compensation.

The processor 12 is configured to calculate a ratio of the number of the emissions of the radiation during scanning of the patient (i.e., emissions from the point source 26) to the number of emissions from the period during which the radioisotope emissions from the patient do not occur or are not detected. The location of the detections on the detector 18 are used to distinguish emissions from the point source 26 and from the patient. The emissions from the point source 26 while emissions occur from the patient are used in the ratio, but the emissions from the patient are not counted for the ratio.

This ratio indicates the scale factor. The ratio indicates count loss fractions due to both system dead time and spectral broadening so that the sensitivity may be normalized. Since the ratio depends on a measurement during patient scanning, the ratio is a real time measure of the system at the time of patient acquisition. In other embodiments, a different function than a ratio is used.

The SPECT system 10 is periodically calibrated. A periodic determination of the count rate/unit activity from the radioisotope is performed (e.g., after the system has undergone or as part of undergoing a monthly calibration). The determination for the given radioisotope is used to set the sensitivity of the detector 18 and/or the SPECT system 10 to the radioisotope. The count rate/unit activity for the radioisotope is determined with no system dead time. Due to dead time during a patient scan, the sensitivity may not be accurate. Spectral broadening may also alter the sensitivity.

The detection of emissions from the point source 26 without the patient occurs during monthly calibrations, but may occur on other days. Due to half-life of radioisotopes used for therapy or imaging in SPECT, the detection likely occurs at a different time than the calibration of the sensitivity. In alternative embodiments, the detection occurs at a same day as the calibration.

The processor 12 is configured to weight the sensitivity as a function of a number of the emissions of the radiation as the compensation. To compensate for dead time, the sensitivity is weighted. Any weighting may be used, such as multiplication or scaling by a ratio of the count rate/unit activity from the source during a patient acquisition to the count rate/unit activity without patient acquisition. This ratio is the normalization factor for system sensitivity. Rather than measuring the system down time and scaling counts, the system sensitivity is normalized based on the count rates to compensate for the dead time. Instead of correcting the sensitivity, the measured projection data or the data model may be corrected using the dead-time compensation factor.

For a given imaging session, a single correction is used. Alternatively, the ratio or scale factor is calculated for different periods, such as different positions of the detector 18 relative to the patient. The counts for each of the periods are corrected based on weights measured for that respective period.

The SPECT system 10, using the processor 12 or another processor, is configured to reconstruct the imaged volume by applying a system matrix or forward projection to the corrected counts. The emissions from the patient, and the sensitivity are used in reconstruction. Any reconstruction may be used to estimate the activity concentration in the patient. The SPECT system 10 accesses the detected emission events from the memory 14 or buffers to reconstruct. Based on the counts for the emission bins from different locations on the detector, the processor 12 is configured to calculate specific uptake values (SUVs) as a function of location in the patient. The counts from the point source 26 are not included in the reconstruction. The SUV at one or more locations are calculated by normalizing the activity concentrations as represented by the counts with a dose for the radioisotope in the patient 22. Alternatively, activity concentration without SUV is used in the reconstruction. The sensitivity is used as part of the iterative reconstruction. For forward projecting, the system or detector sensitivity and point spread function are applied.

The detected emission events, other functional information, or other scan data are stored in the memory 14. The data is stored in any format. The memory 14 is a buffer, cache, RAM, removable media, hard drive, magnetic, optical, database, or other now known or later developed memory. The memory 14 is a single device or group of two or more devices. The memory 14 is part of SPECT system 10 or a remote workstation or database, such as a PACS memory.

The memory 14 may store data at different stages of processing, such as a count of emissions from the point source 26 without the patient, a count of emissions from the point source 26 while also detecting emissions from the patient, a count of emissions from the patient, energy region of interest, sensitivity, raw data (e.g., energy and location) representing detected emissions from the patient without further processing, filtered or thresholded data prior to reconstruction, reconstructed data, filtered reconstruction data, a system matrix, forward projection information, projection data, thresholds, an image to be displayed, an already displayed image, or other data. The memory 14 or a different memory stores the ratio or other scale factor for compensating for dead time. For processing, the data bypasses the memory 14, is temporarily stored in the memory 14, or is loaded from the memory 14.

The memory 14 is additionally or alternatively a non-transitory computer readable storage medium with processing instructions. The memory 14 stores data representing instructions executable by the programmed processor 12. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 16 is a CRT, LCD, plasma screen, projector, printer, or other output device for showing an image or quantity. The display 16 displays an image of the reconstructed patient volume, such as showing activity concentration as a function of location. The uptake function (e.g., SUV) of the tissues of the patient may be represented in the image. Multi-planar reconstruction, 3D rendering, or cross-section imaging may be used to generate the image from the voxels of the reconstructed volume. Alternatively or additionally, any quantities derived by the processor 12 may be displayed, such as SUVs and/or change in SUV. Other quantities may be determined, such as average SUV or activity concentration for a region, maximum SUV, peak SUV in a predetermined unit volume, variance in activity concentration, or total SUV. The image values or quantity is based on counts and adapted sensitivity. The image values or quantity are compensated for dead time.

FIG. 3 shows one embodiment of a method for dead time compensation for a gamma camera or other emission detector. The method normalizes sensitivity of the emission detector to compensate for dead time. A point source with a companion radioisotope to the one used for emissions from the patient is used. Emissions from the point source are detected while and while not detecting emissions from the patient. A ratio of point source counts may be used to normalize the sensitivity, which compensates for dead time.

The method is implemented by the system of FIG. 1, the arrangement of FIG. 2, both, or other system and arrangement. A processor performs acts 38-46. A gamma camera or detector and detector electronics perform acts 30 and 32. A vessel or point source with a radioisotope is used for performing acts 30 and 32. A radiotracer is used to perform act 32. Other devices or materials may be used or controlled to perform any of the various acts.

Additional, different, or fewer acts may be performed. For example, act 30 is not performed where the number of emissions from the point source during a black scan (i.e., no patient) is known or simulated. As another example, acts 44 and/or 46 are not provided. In other examples, acts related to positioning the patient, configuring the SPECT scanner, and/or SPECT imaging are provided. The acts are performed in the order shown or a different order.

In act 30, emissions from a point source with a radioisotope are detected. A gamma camera or other detector detects emissions from a shielded source positioned by the detector (e.g., connected to a corner of the detector). During a time in which emissions from other radioisotopes are not also being purposefully detected, emissions from the shielded point source are detected. A blank scan is performed using the point source. The blank scan occurs without emissions from the patient and/or not during a patient scan.

A count over time or rate of emission is determined. The determination is made while the detector and electronics are not subjected to dead time. The emissions are measured to establish a base line count rate. In alternative embodiments, the count rate from the point source is simulated. The count rate is stored and later loaded from memory.

The emissions of the blank scan are detected with the radioisotope being a same one as used or to be used for the patient. The strength of the radioisotope in the point source is less than used for the radiopharmaceutical, such as being less by a factor of at least 2 (i.e., being less than half).

The detection applies an energy filter. The energy filter distinguished emissions from the radioisotope from other emissions to determine a factor to normalize the system specific sensitivity measured at low count rates where the system dead time is negligible.

A region of interest of the point response function of the detector to the radioisotope is determined. The region of interest may be a predetermined, default, user set, or adaptive range of point response. A central region of interest is used to compute the count rate/unit activity upon reconstruction. The same region of interest is used for the emissions from the point source during the patient scan.

In act 32, emissions are detected during a scan of a patient. During the scan, the gamma camera or other detector detects emissions from any source. The emissions are from the radioisotope in the point source and from a radioisotope in the patient. The emissions from the point source are detected at a corner or other position relative to the detector. By placing a shielded source to direct emissions to the detector, the emissions may be detected. The radioisotope in the patient is an injected or ingested liquid tracer. Emissions from the different sources are detected during the scan of the patient.

The emissions from both sources during the patient scan are subjected to dead time. During the time in which a patient is scanned (i.e., while the patient is positioned for scanning), the emissions are detected in real-time. As the emissions from the patient and the point source occur, at least some of the emissions are detected. Due to the greater number of emissions occurring while scanning the patient as compared to act 30, more spectral broadening may occur.

Emissions from the patient are separated from the emissions from the point source. The location of the detected emissions are used to separate. Due to known position of the point source relative to the detector, the spatial location of detected emissions may be used to distinguish emissions from the point source from emissions from the patient. A same spatial region of interest on the detector is used in acts 30 and 32 to detect emissions from the point source.

So that the point source counts from the blank scan and the patient scan are more reliably comparable, a same energy window is used for both. The same radioisotope is used, allowing the energy window and region of interest of the point spread function to be the same. The detection electronics threshold or window energies within a default, user set, or predetermined range. One range is provided for detecting emissions from the radioisotope in the patient and emissions from the point source.

The same region of interest in the point response function is used for data acquired during a patient scan with the companion source (i.e., point source with the same radioisotope). For data from during the patient scan using the same radioisotope, the extended regions of the point response function for the companion source may be contaminated by photons emanating from the patient, so applying the same region of interest reduces this contamination.

Since the companion source is the same isotope as the radiopharmaceutical and in turn has the same emission energy, fully integrated mode of operation is not needed. Pile-up processing may be applied. In other embodiments, the fully integrated mode of operation is used.

The processor or detection electronics determine counts and/or count rates for the emissions from the sources during the patient scan. The number of emissions or number over a period per source are calculated. As the radioisotope in the patient and the point source decays, gamma radiation is emitted. The gamma camera detects the emissions. The emissions may occur at a same time or different times. Each detected emission results in dead time. Any following or subsequent emissions occurring in the dead time are not detected. The detection of the emissions continues during the patient scan with some emissions being missed.

In act 38, sensitivity is corrected. A processor increases or decreases the sensitivity. The calibrated system or detector sensitivity for the radioisotope being used is altered, compensating for the dead time. The correction adapts the sensitivity used for reconstruction from the detected emissions from the patient.

The correction is a function of the point source count rates from acts 30 and 32. The count rate from the blank scan (i.e., the count from the point source without emissions from the patient) and/or the count rate from the patient scan (i.e., the count from the point source emissions) are used in the correction. For the patient scan, the count from the point source subject to the dead time but not including counts from the patient are used. The counts are distinguished based on the location of detection on the gamma camera.

Act 38 as represented in FIG. 3 includes acts 40 and 42. Additional, different, or fewer acts may be performed to correct the sensitivity.

In act 40, the processor calculates a ratio of the count rate from the point source during patient acquisition to the count rate from the point source of the blank scan. The count rate per unit activity is used, so that the sensitivity may be adapted.

In act 42, the processor normalizes the sensitivity. The system or detector sensitivity is normalized to compensate for the dead time. The counts from the point source are used in the normalization. The sensitivity is multiplied by the ratio. The effects of spectral broadening due to the greater number of counts during patient scanning are reduced by adapting the sensitivity. This also compensates for the dead time, but without determining an amount of dead time and/or altering the count of emissions from the patient. The amount of dead time may be calculated and a separate count rate correction applied. The measured projection data or the data model may be corrected using the ratio.

In act 44, the processor calculates the activity concentration. The counts from the patient-based emissions are used to estimate the activity at a given location or region in the patient. The activity concentration in a patient having received the liquid radiotracer is determined as part of reconstruction by the SPECT system. After ingesting or injecting the radiotracer into the patient, the patient is positioned relative to the detector and/or the detector is positioned relative to the patient. Emissions from the radiotracer within the patient are detected over time. To determine the locations within the patient at which the emissions occurred, the detected emissions are reconstructed into an object space.

For reconstruction, the activity concentration (e.g., quantitative SPECT) is reconstructed using a system matrix or forward projection. The system matrix or forward projection includes one or more calculations using the adapted system sensitivity. Distribution of emissions in a volume or image data is reconstructed from the detected emissions. The quantity or amount of uptake for each location (e.g., voxel) may be estimated as part of the reconstruction in computed tomography. The SPECT system estimates the activity concentration of an injected radiopharmaceutical or tracer for the different locations. In quantitative SPECT, the goal is to estimate the activity concentration in kBq/ml of the tracer (i.e., isotope) that was injected into and distributed within the patient.

The reconstruction is iterative and contains a model of the imaging formation physics as a pre-requisite of quantitative reconstruction. The image formation model includes the detected data (e.g., corrected counts), the system matrix or forward projection, isotope properties (e.g., dose value), and/or biology. The system matrix or forward projection represents mechanical properties of system such as adapted system or detector sensitivity and point response function, but may include other information (e.g., injection time and patient weight as represented by SUV).

Reconstruction includes a projection operator that is able to simulate a given SPECT system or SPECT class. Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, NNLS, or another approach.

Specific uptake values (SUVs) may be calculated. The activity concentration represents the amount of uptake at each location. This amount of uptake is a measure of emitted radiation, so is not normalized for the radiation dose provided to the patient. As a result, comparing uptake from different times may not be useful unless the same dose is provided. By calculating the SUV, uptake normalized for dose is provided, allowing comparison of different measures.

In act 46, a SPECT image is generated. Where quantitative SPECT is not provided, the counts may be used without SUV and/or activity concentration calculation. For either quantitative or qualitative SPECT, the counts are used to reconstruct the emissions as a function of location. The relative amounts of emissions from different locations are reconstructed using the corrected sensitivity.

The reconstructed emission distribution is imaged. Any imaging may be used, such as extracting a planar representation from voxels representing the distribution. A multi-planar reconstruction may be generated. In one example, a three-dimensional rendering using projection or surface rendering is performed. The resulting three-dimensional representation is displayed on the two-dimensional screen.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for dead time compensation for a gamma camera, the method comprising:
   detecting, with the gamma camera, a first count rate from a calibrated radioisotope source connected adjacent to and directed at the gamma camera, the detecting of the first count rate being performed without emissions from a patient;
   detecting, with the gamma camera, a second count rate from the radioisotope source or another radioisotope source, the detecting of the second count rate being performed during detection of the emissions from within a patient, the emissions being from a same radioisotope as the radioisotope source but within the patient;
   correcting a sensitivity as a function of the first and second count rates;
   reconstructing from the emissions as a function of the corrected sensitivity; and
   generating an image from the reconstructing.

2. The method of claim 1 wherein detecting the first and second count rates comprises detecting with the radioisotope source being a shielded source connected to emit at a corner of the gamma camera.

3. The method of claim 1 wherein detecting the first and second count rates comprises detecting with the radioisotope within the patient and the radioisotope source having a same radiopharmaceutical.

4. The method of claim 1 wherein detecting the first and second counts comprises detecting in a same region of interest of a point response function of the gamma camera for both the first and second counts.

5. The method of claim 1 wherein detecting the first and second counts comprises detecting the first and second counts in a same energy window.

6. The method of claim 1 wherein detecting the first count comprises detecting with the radioisotope source having a strength less than the radioisotope within the patient by a factor of at least two.

7. The method of claim 1 wherein correcting the sensitivity comprises calculating a ratio of the second count rate to the first count rate.

8. The method of claim 1 wherein correcting comprises normalizing the sensitivity, the sensitivity being a system sensitivity.

9. The method of claim 1 wherein generating the image comprises generating a single photon emission computed tomograph image.

10. A single photon emission computed tomography (SPECT) system comprising:
    a gamma camera;
    a shielded and calibrated point source connected at the gamma camera to emit radiation directed at the gamma camera from a radioisotope in the shielded point source;
    detection electronics configured to detect emissions, including the radiation from the shielded and calibrated point source and radioisotope emissions from a patient, the radioisotope emissions from the patient being from a same radioisotope as the radioisotope in the shielded point source; and
    a processor configured to compensate for dead time of the detection electronics, the compensation being a function of real-time detection of the radiation from the shielded and calibrated point source.

11. The SPECT system of claim 10 wherein the shielded point source connects to the gamma camera with a hole in a shield directed to the gamma camera.

12. The SPECT system of claim 10 wherein the radioisotope of the shielded point source has a strength less than the radioisotope from the patient by a factor of at least ten.

13. The SPECT system of claim 10 wherein the detection electronics are configured to detect the radiation from the shielded point source with an energy window for a range of energies the same as for the radioisotope emissions from the patient.

14. The SPECT system of claim 10 wherein the detection electronics are configured to detect the emissions, including the radiation and the radioisotope emissions, during a scanning session for a patient.

15. The SPECT system of claim 10 wherein the processor is configured to calculate a ratio of a first number of the emissions of the radiation to a second number from a period during which the radioisotope emissions do not occur.

16. The SPECT system of claim 10 wherein the processor is configured to weight a sensitivity as a function of a number of the emissions of the radiation as the compensation.

17. The SPECT system of claim 10 wherein the calibrated point source is located in the field of view of the gamma camera.

18. A method for correction of an emission detector, the method comprising:
    detecting, with a detector, first emissions from a patient and second emissions from a point source connected adjacent to the detector, the second emissions subjected to dead time from the detection of the first emissions and the first and second emissions being from a same radioisotope; and
    adapting, by a processor, for a reconstruction from the first emissions, the adapting being a function of a count of the second emissions.

19. The method of claim 18 wherein detecting comprises detecting the first and second emissions in real-time during a patient scan;
    further comprising detecting third emissions from the point source, the detecting of the third emissions not occurring during the patient scan;
    wherein adapting comprises normalizing sensitivity as a function of the count of the second emissions and a count of the third emissions.

20. The method of claim 19 wherein detecting the second and third emissions comprises detecting with a same energy window.

21. The method of claim 18 further comprising reconstructing a distribution of the first emissions with a sensitivity as adapted in the adapting.

22. A method for dead time compensation for a gamma camera, the method comprising:
    detecting, with the gamma camera, a first count rate from a calibrated radioisotope source connected adjacent to the gamma camera, the detecting of the first count rate being performed without emissions from a patient;
    detecting, with the gamma camera, a second count rate from the radioisotope source or another radioisotope source, the detecting of the second count rate being performed during detection of the emissions from within a patient, the emissions being from a same radioisotope as the radioisotope source but within the patient;
    correcting a sensitivity as a function of the first and second count rates;
    reconstructing from the emissions as a function of the corrected sensitivity; and
    generating an image from the reconstructing,
    wherein detecting the first count comprises detecting with the radioisotope source having a strength less than the radioisotope within the patient by a factor of at least two.

23. A single photon emission computed tomography (SPECT) system comprising:
    a gamma camera;
    a shielded and calibrated point source connected at the gamma camera to emit radiation from a radioisotope in the shielded point source;
    detection electronics configured to detect emissions, including the radiation from the shielded and calibrated point source and radioisotope emissions from a patient, the radioisotope emissions from the patient being from a same radioisotope as the radioisotope in the shielded point source; and
    a processor configured to compensate for dead time of the detection electronics, the compensation being a function of real-time detection of the radiation from the shielded and calibrated point source,
    wherein the radioisotope of the shielded point source has a strength less than the radioisotope from the patient by a factor of at least two.

24. A method for correction of an emission detector, the method comprising:
    detecting, with a detector, first emissions from a patient and second emissions from a point source, the second emissions subjected to dead time from the detection of the first emissions and the first and second emissions being from a same radioisotope; and
    adapting, by a processor, for a reconstruction from the first emissions, the adapting being a function of a count of the second emissions,
    wherein the radioisotope of the point source has a strength less than the radioisotope from the patient by a factor of at least two.

* * * * *